(12) United States Patent
Schermeier et al.

(10) Patent No.: US 10,617,835 B2
(45) Date of Patent: Apr. 14, 2020

(54) PATIENT CONNECTION FOR THE ARTIFICIAL RESPIRATION OF A PATIENT

(71) Applicant: Drägerwerk AG & Co. KGaA, Lübeck (DE)

(72) Inventors: Olaf Schermeier, Lübeck (DE); Götz Kullik, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 156 days.

(21) Appl. No.: 15/393,864

(22) Filed: Dec. 29, 2016

(65) Prior Publication Data

US 2017/0106156 A1 Apr. 20, 2017

Related U.S. Application Data

(63) Continuation of application No. 11/950,589, filed on Dec. 5, 2007, now abandoned.

(30) Foreign Application Priority Data

Feb. 17, 2007 (DE) .......................... 10 2007 007 969

(51) Int. Cl.
*A61B 5/08* (2006.01)
*A61M 1/00* (2006.01)
(Continued)

(52) U.S. Cl.
CPC ........ *A61M 16/0003* (2014.02); *A61M 16/01* (2013.01); *A61M 16/08* (2013.01); *A61M 16/0833* (2014.02); *A61M 16/0875* (2013.01); *A61M 16/107* (2014.02); *A61M 16/1065* (2014.02); *A61M 16/0465* (2013.01); *A61M 16/06* (2013.01); *A61M 16/1055* (2013.01); *A61M 2016/0027* (2013.01); *A61M 2205/14* (2013.01); *A61M 2205/3368* (2013.01); *A61M 2205/3569* (2013.01); *A61M 2205/3592* (2013.01); *A61M 2205/60* (2013.01); *A61M 2205/6018* (2013.01); *A61M 2205/6054* (2013.01); *A61M 2230/04* (2013.01); *A61M 2230/205* (2013.01); *A61M 2230/40* (2013.01);
(Continued)

(58) Field of Classification Search
None
See application file for complete search history.

(56) References Cited

U.S. PATENT DOCUMENTS

2003/0135124 A1* 7/2003 Russell ............. A61B 5/02007
  600/500
2004/0182392 A1* 9/2004 Gerder ................. A61M 16/08
  128/204.22
(Continued)

*Primary Examiner* — Michael R Bloch
(74) *Attorney, Agent, or Firm* — McGlew and Tuttle, P.C.

(57) ABSTRACT

A breathing gas-carrying patient connection (2) for the artificial respiration of a patient (1) by an anesthesia apparatus or respirator (3) with one or more sensors (9, 10, 11) for detecting patient-relevant measured variables and with a telemetric transmission of the sensor data from the patient connection (2) to a machine-side connection element (13) for the patient connection (2), wherein the telemetric transmission of the sensor data is designed for wireless bidirectional communication between the patient connection (2) and the connection element (13), makes possible the reliable transmission of data into the machine-side connection element (13).

19 Claims, 2 Drawing Sheets

(51) Int. Cl.
*A61M 16/00* (2006.01)
*A61M 16/08* (2006.01)
*A61M 16/10* (2006.01)
*A61M 16/01* (2006.01)
A61M 16/04 (2006.01)
A61M 16/06 (2006.01)

(52) U.S. Cl.
CPC ..... *A61M 2230/50* (2013.01); *A61M 2230/65* (2013.01)

(56) References Cited

U.S. PATENT DOCUMENTS

| | | | | |
|---|---|---|---|---|
| 2005/0245836 | A1* | 11/2005 | Star | B82Y 10/00 257/253 |
| 2007/0062533 | A1* | 3/2007 | Choncholas | A61M 16/024 128/204.23 |
| 2008/0078387 | A1* | 4/2008 | Vandine | A61M 16/04 128/204.21 |
| 2008/0078388 | A1* | 4/2008 | Vandine | A61M 16/04 128/204.21 |

* cited by examiner

PATIENT CONNECTION FOR THE ARTIFICIAL RESPIRATION OF A PATIENT

CROSS REFERENCE TO RELATED APPLICATIONS

This application is a continuation under 37 CFR 1.53(b) of pending prior U.S. patent application Ser. No. 11/950,589 filed Dec. 5, 2007, which claims the benefit of priority of German Patent Application DE 10 2007 007 969.0 filed Feb. 17, 2007, the entire contents of each application are incorporated herein by reference.

FIELD OF THE INVENTION

The present invention pertains to a breathing gas-carrying patient connection for the artificial respiration of a patient.

BACKGROUND OF THE INVENTION

The measurement of physiological variables, for example, the airway pressure and the flow through the airways, the breathing gas temperature, the body core temperature, the oxygen saturation and ECG (Electrocardiogram) are of great significance for the therapy of patients with respiration support, hereinafter called generally artificial respiration. These measurements are carried out, in general, with individual sensors at individual cables independently from the breathing tubes for the respiration support.

The treatment parameters and data arising for a certain patient from the type of the patient connection are entered manually by the attending staff in the respiration support device, i.e., especially an anesthesia apparatus or a respirator.

The individual sensors used with their cables lead to error-prone and cluttered situations in hospitals (so-called "spaghetti syndrome"), and the need to enter device data and therapy data takes time and requires attention on the part of the attending staff. A tube with a device for detecting the endotracheal pressure and the breath flow is disclosed in DE 199 51 578 C1. In this device a differential pressure sensor is arranged in a liquid-proof manner in the tube wall close to the tip of the tube and a differential pressure sensor is arranged close to the base and the two sensors are coupled pneumatically via a duct in the tube wall. This duct is connected to the atmosphere via an opening. A transmitter is provided for the telemetric transmission of the measured data.

SUMMARY OF THE INVENTION

The object of the present invention is to provide a breathing gas-carrying patient connection for the artificial respiration of a patient, which detects, on the one hand, various patient-relevant measured variables in a non-invasive manner and, on the other hand, makes possible the reliable transmission of data directly from the patient connection into a machine-side connection element.

According to the invention, a patient connection device is provided for the artificial respiration of a patient with an anesthesia apparatus or respirator having a machine-side connection element. The patient connection device may comprise a patient connection element for applying to an air passage of a patient. One or more sensors may be located on the patient connection element for detecting patient-relevant measured variables. A telemetric transmission means may be provided for telemetrically transmitting the patient-relevant measured variables from the patient connection element to the machine-side connection element such that the respirator receives the patient-relevant measured variables. The sensor data transmission means may be in bidirectional communication with the patient connection element and the machine-side connection element.

The patient-relevant measured variables may include identification information.

The telemetric transmission means may change the identification information.

The telemetric transmission means may wirelessly transmit energy from the connection element into the patient connection such that the one or more sensors are powered via the wireless energy transmission.

The patient connection may further comprise an energy storage means and/or a data memory.

The patient connection element may be an endotracheal tube, a tracheotomy cannula or a full face, nasal or larynx mask.

The connection element may comprise at least one Y-piece, a breathing tube or a breathing system.

The telemetric transmission means may be designed as inductive or capacitive elements.

At least one of the sensors may be a temperature sensor, an oxygen saturation sensor, a pulmonary internal pressure sensor and/or an electrode.

One or more electrodes may be provided. The one or more electrodes may be an electrocardiogram (ECG) electrode or an electroimpedance tomography (EIT) electrode.

According to the invention, a device for the artificial respiration of a patient is provided. The device may comprise a respirator with a respirator connection receiver portion. A patient connection insertion element may be connected to the respirator connection receiver portion. The patient connection insertion element may have a patient insertion end in contact with the patient. A sensor may be located at the patient insertion end of the patient connection insertion element. The sensor may sense a patient parameter to define patient sensor data. A wireless telemetric transmission means may be provided for wireless bidirectional telemetric communication between the patient connection insertion element and the respirator connection receiver portion such that the patient sensor data passes from the sensor located at the patient insertion end to the respirator connection receiver portion. The respirator may receive the patient sensor data.

The patient insertion end of the patient connection insertion element may have an inflatable gasket. The sensor may be a temperature sensor for measuring a body core temperature of the patient. The temperature sensor may be located on an outer surface of the inflatable gasket. The inflatable gasket may be in an inflated state when the patient connection insertion element is in contact with the patient. The temperature sensor may be in contact with the patient when the inflatable gasket is in the inflated state.

The wireless telemetric transmission means may include a first antenna located within the patient connection insertion element and a second antenna located within the respirator connection receiver portion. The first antenna may be located at an end of the patient connection insertion element opposite the patient insertion end. The first antenna may be opposite the second antenna.

The second antenna may be electrically connected to the respirator via a first electric line extending within the respirator connection receiver portion. The sensor may be electrically connected via a second electric line. The second electric line may extend within the patient connection insertion element from the first antenna to the sensor.

The device may comprise an electrode. The electrode may be one of an electroimpedance tomography electrode, an electrocardiogram electrode and an impedance cardiography electrode. The electrode may be located on the outer surface of the inflatable gasket opposite the temperature sensor. The electrode may be in contact with the patient when the inflatable gasket is in the inflated state.

The device may further comprise a breathing gas humidifier and a plurality of bacteria filters. The respirator connection element may include a Y-piece connection element having a first branch connection portion and a second branch connection portion. The second antenna may be located within the first branch connection portion. One of the bacteria filters may be connected to the first branch connection portion. Another of the bacteria filters may be connected to the second branch connection portion. The breathing gas humidifier may be connected to the second branch connection portion.

The device may further comprise a data storage and energy means for storing energy and for storing the patient sensor data. The patient data may include manufacturing data of the patient connection insertion element and information relating to a number of uses of the patient connection insertion element.

The wireless telemetric transmission means may wirelessly transmit energy from the respirator connection receiver portion to the patient connection insertion element such that the sensor is powered via the wireless energy transmission.

The patient connection insertion element may be an endotracheal tube, a tracheotomy cannula or a full face, nasal or larynx mask.

According to the invention, a device is provided for the artificial respiration of a patient. The device may comprise a respirator and a patient respirator connection structure connecting the respirator to the patient. The patient respirator connection structure may have a patient receiving portion and a respirator connection portion. The respirator connection portion may be connected to a machine side of the respirator. The patient receiving portion may be in contact with the patient. A plurality of sensors may be located at an end of the patient receiving portion. Each sensor may sense a patient parameter to define patient sensor data. A wireless telemetric transmitter may be provided for telemetrically transmitting the patient sensor data from the plurality of sensors located on the patient receiving portion to the respirator connection portion such that the respirator receives the patient sensor data. The wireless telemetric transmitter may be in bidirectional communication with the plurality of sensors located on the patient receiving portion and the respirator. A display means may be provided for displaying the patient sensor data.

An essential advantage of the present invention is that a breathing gas-carrying patient connection follows from the structural integration of different sensors and the preferred integration of a data memory and preferably of an energy storage means with a corresponding interface for data and energy between the patient connection and the anesthesia apparatus or respirator performing the artificial respiration.

A breathing gas-carrying patient connection is defined especially as an endotracheal tube, called "tube" for short, a tracheotomy cannula or a full face, nasal or larynx mask used for the respiration.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
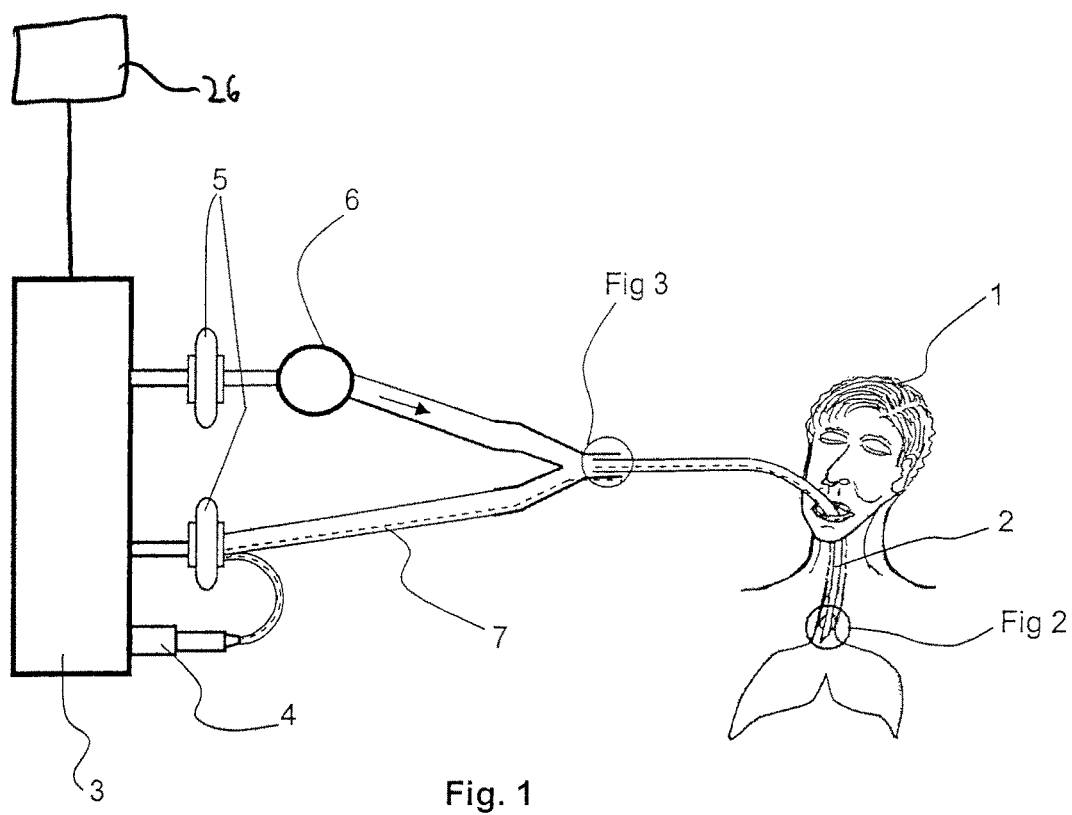
FIG. 1 is a schematic view showing an intubated patient connected to a respirator.
Figure 2:
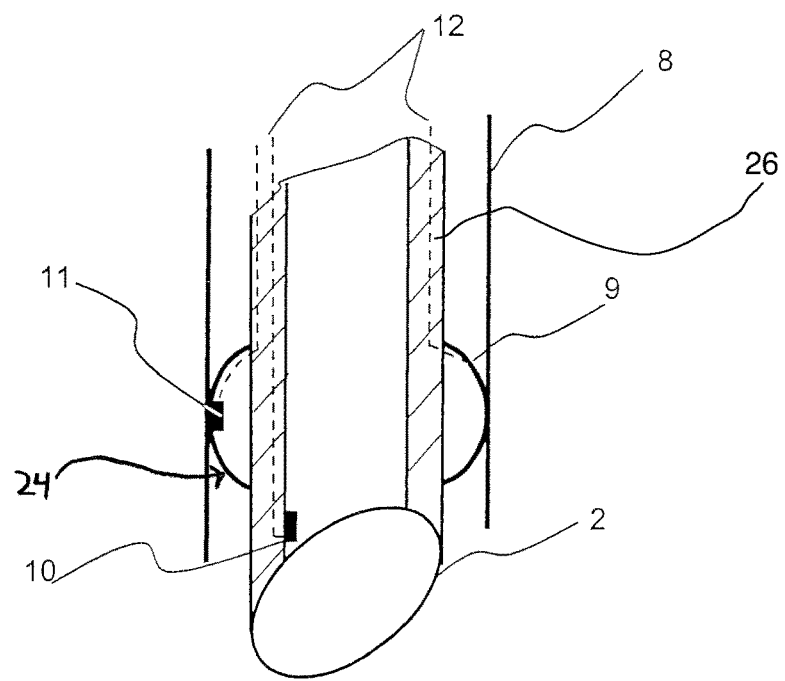
FIG. 2 is a cross sectional view showing a detail through the tip of the tube.

Referring to the drawings in particular, FIG. 1 shows a patient 1 with a patient connection 2 designed as a tube in the trachea 8 (FIG. 2). The sensor data and electric energy are transmitted in a contactless and field-based manner into and from the respirator 3 via the first electric line 7 in the expiration branch, because an active breathing gas humidifier 6 is inserted in the inspiration branch. The inspiration branch and the expiration branch are equipped with bacteria filters 5. The respirator 3 is, for example, a home respirator. The data transfer into the respirator 3 is carried out by means of a plug-type contact 4 or, as an alternative, likewise in a field-based and contactless manner, especially inductively. A display 26 is connected to the respirator 3 to display patient sensor data.

FIG. 2 shows a sectional view of a detail through the tip of the patient connection 2 designed according to this embodiment as a tube in the trachea 8 of the patient 1. A sensor is a pulmonary internal pressure sensor 10, which according to this embodiment is arranged on the inside of the tube in order to perform the measurement there possibly unaffected by body fluids that are present. The temperature sensor 11 for measuring the body core temperature is placed on the outside of the inflatable gasket 24 of the tube in order to have optimal contact with the body tissue there. An ECG electrode is likewise positioned on the outside of the inflatable gasket of the tube. The electrode 9 may also be one of several ECG electrodes. The electrode 9 may also be an EIT (electroimpedance tomography) electrode, which is used, e.g., to supply electric power or as a counterelectrode in an Err system. The at least one electrode 9 may also be used for impedance cardiography (ICG), which is known per se. The second electric line 12 in the tube wall is used to derive the sensor signals and to send energy to the sensors.

Figure 3:
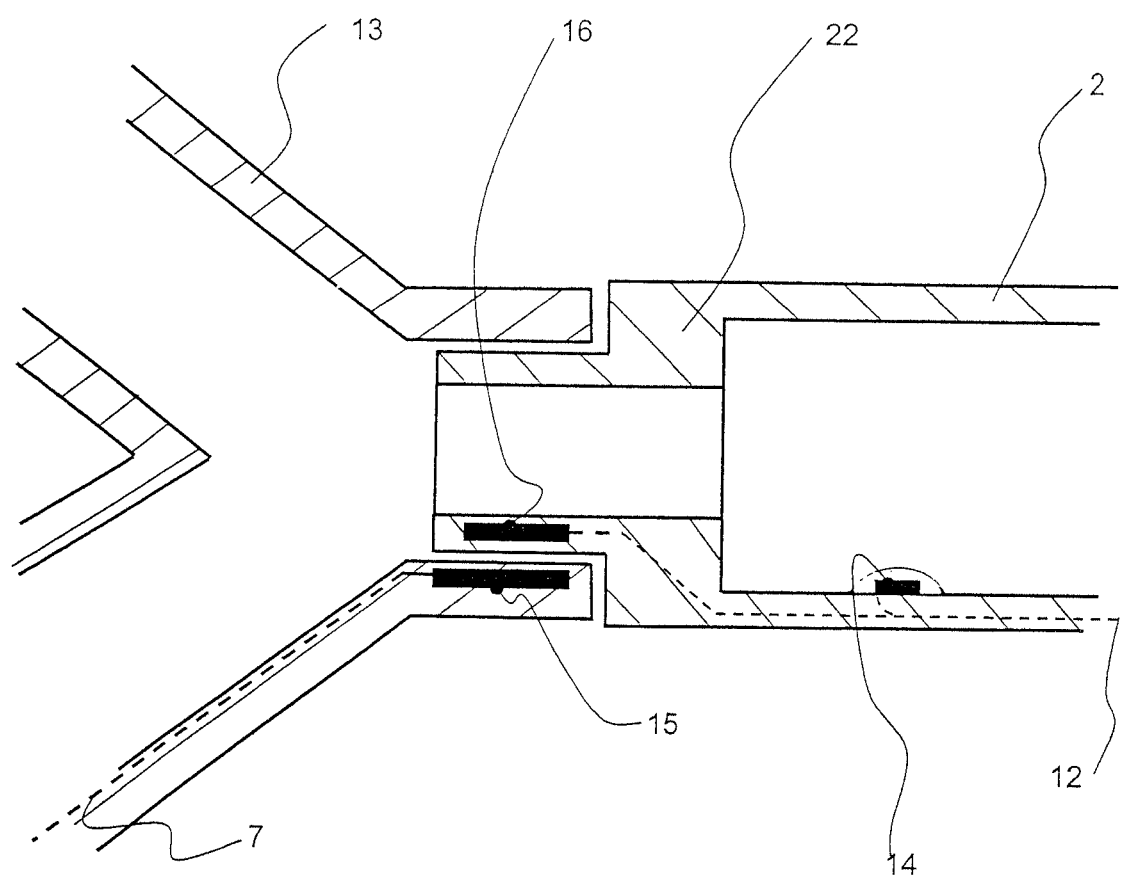
FIG. 3 is a cross sectional view showing a detail through the electrically non-conductive antenna connection between the tube connector and the Y-piece.

FIG. 3 shows a sectional view of a detail through the electrically non-conductive, preferably inductive antenna connection between the tube connector 22 and the connection element 13, which is designed as a Y-piece here. The antenna connection is established by means of the first antenna 15 in the Y-piece and the second antenna 16 in the tube connector 22. The data memory and energy storage means 14 is located in the tube and is connected to the second antenna 16 and to the sensors by means of the second electric line 12. The electric lines 7 and 12 are preferably integrated in the wall of the expiration branch or of the tube. Sensor data containing identification information, such as static specific data on the patient connection 2 itself, for example, geometric or physical characteristics, information on use, manufacturer data, manufacturing and shelf life data, etc., as well as variable information, for example, patient data, respiration parameters and information on the preparation performed in case of multiple usability of the patient connection 2, may be stored in the data memory and energy storage means 14. The sensor data optionally contain information on the measured patient data during a time period during which the antenna connection was interrupted (data logger function). The energy storage means is also used especially for the temporary operation of the sensors 9, 10, 11 when the line connection to the respirator 3 is interrupted, for example, when the patient 1 shall be connected to another respirator 3. An additional energy storage means in the form of a miniaturized battery or a capacitor with very high capacity may optionally be provided.

It is especially advantageous to use the electromagnetically operated transponder technique by means of so-called RFID (Radio Frequency Identification) tags.

The antenna connection between the tube or the tube connector 22 and the connection element 13 to the respirator 3, which the connection element is designed as a Y-piece here, contains especially coils, capacitors for magnetic, electromagnetic and/or capacitive coupling. Optical elements are also suitable, in principle, for a non-conductive coupling and transmission. It is essential that the data and energy transmission take place in a contactless manner exclusively by field effects. As a result, all electrically conductive elements are hermetically encapsulated, so that they are nonsusceptible to all fluids in the patient 1 and can be subjected to all the hygienic procedures practiced in routine clinical practice, for example, washing in a dishwasher and/or disinfection by wiping with aqueous preparations in a very simple manner. In addition, advantages arise for electric safety, for example, compatibility with defibrillators.

While specific embodiments of the invention have been shown and described in detail to illustrate the application of the principles of the invention, it will be understood that the invention may be embodied otherwise without departing from such principles.

What is claimed is:

1. A patient connection arrangement for artificial respiration of a patient with an anesthesia apparatus or respirator having a machine-side connection element, the patient connection arrangement comprising:
   a patient connection for applying to an air passage of the patient, where the patient connection includes a tube;
   one or more sensors located on said patient connection for measuring patient-relevant variables;
   a telemetric transmission means for telemetrically transmitting said patient-relevant variables from said patient connection to said machine-side connection element such that said anesthesia apparatus or said respirator receives said patient-relevant variables, said telemetric transmission means being in bidirectional communication with said patient connection and said machine-side connection element;
   an energy storage arranged on said patient connection and being configured to store energy when said telemetric transmission means are connected to said anesthesia apparatus or respirator, and providing energy when said telemetric transmission means are interrupted; and
   a data storage arranged on said patient connection and being configured to store sensor data, said sensor data including variable information and static data, said data storage being integrated with said telemetric transmission means and configured to be part of transferring of data between the patient connection and the anesthesia apparatus or respirator, the transferring also going through the telemetric transmission means, said sensor data including patient-relevant variables information on patient data measured by said one or more sensors during a time period during which said telemetric transmission means was interrupted;
   wherein the energy storage and the data storage are located on a sidewall of the tube, and electrically connected to the telemetric transmission means and the one or more sensors.

2. A patient connection arrangement in accordance with claim 1, wherein: said variable information includes patient data, respiration parameters and information on preparation performed in case of multiple usability of the patient connection.

3. A patient connection arrangement in accordance with claim 1, wherein:
   said static data includes one of geometric characteristics, physical characteristics, information on use, manufacturer data, manufacturing and shelf life data.

4. A patient connection arrangement in accordance with claim 1, wherein:
   said variable information includes information on preparation performed in case of multiple usability of the patient connection.

5. A patient connection arrangement in accordance with claim 1, wherein said telemetric transmission means is designed as inductive or capacitive elements.

6. A patient connection arrangement, the patient connection arrangement comprising:
   one of an anesthesia apparatus or respirator;
   a patient connection including a tube having a first end configured to connect to a branch of one of the anesthesia apparatus or the respirator, said patient connection having a second end configured to apply air to a patient;
   one or more sensors located on said patient connection for measuring patient-relevant variables;
   a telemetric transmitter on said patient connection telemetrically transmitting said patient-relevant variables from said patient connection to the branch of the one of the anesthesia apparatus or respirator for transfer of said patient-relevant variables to the one of the anesthesia apparatus or respirator along the branch, said telemetric transmitter being in bidirectional communication with the one of the anesthesia apparatus or respirator through the branch;
   an energy storage arranged on said patient connection and being configured to store energy when said telemetric transmitter is connected to said one of anesthesia apparatus or respirator, and providing energy when said telemetric transmitter is interrupted; and
   a data storage arranged on said patient connection and being configured to store sensor data, said sensor data including variable information and static data, said data storage being integrated with said telemetric transmitter and configured to be part of transferring of data between the patient connection and the one of the anesthesia apparatus or respirator, the transferring also going through the telemetric transmission means, said sensor data including patient-relevant variables measured by said one or more sensors during a time period during which said telemetric transmitter was interrupted;

wherein the energy storage and the data storage are located on a sidewall of the tube, and are electrically connected to the telemetric transmitter and the one or more sensors.

7. A patient connection arrangement in accordance with claim 6, wherein:
said variable information includes patient data.

8. A patient connection arrangement in accordance with claim 6, wherein: said variable information includes respiration parameters.

9. A patient connection arrangement in accordance with claim 6, wherein:
said variable information includes information on preparation performed in case of multiple usability of the patient connection.

10. A patient connection arrangement in accordance with claim 6, wherein:
said variable information includes patient data, respiration parameters and information on preparation performed in case of multiple usability of the patient connection.

11. A patient connection arrangement in accordance with claim 10, wherein:
said static data includes one of geometric characteristics, physical characteristics, information on use, manufacturer data, manufacturing and shelf life data.

12. A patient connection arrangement in accordance with claim 6, wherein:
said static data includes geometric characteristics of said patient connection.

13. A patient connection arrangement in accordance with claim 6, wherein:
said static data includes physical characteristics of said patient connection.

14. A patient connection arrangement in accordance with claim 6, wherein:
said static data includes information on use of said patient connection.

15. A patient connection arrangement in accordance with claim 6, wherein:
said static data includes manufacturer data of said patient connection.

16. A patient connection arrangement in accordance with claim 6, wherein:
said static data includes manufacturing and shelf life data of said patient connection.

17. A patient connection arrangement in accordance with claim 6, wherein:
said static data includes one of geometric characteristics, physical characteristics, information on use, manufacturer data, manufacturing and shelf life data.

18. A patient connection arrangement in accordance with claim 6, wherein: said data storage is configured to perform data logging of the patient relevant variables measured by said one or more sensors during the time period.

19. A patient connection arrangement in accordance with claim 6, wherein:
said sensor data includes information relating to a number of uses of said patient connection.

* * * * *